US009554819B2

(12) United States Patent
Suzuki et al.

(10) Patent No.: US 9,554,819 B2
(45) Date of Patent: Jan. 31, 2017

(54) ENDOSCOPE TREATMENT TOOL (71) Applicant: OLYMPUS CORPORATION, Tokyo (JP)

(72) Inventors: Keita Suzuki, Tokyo (JP); Masatoshi Sato, Yokohama (JP)

(73) Assignee: OLYMPUS CORPORATION, Tokyo (JP)

( * ) Notice: Subject to any disclaimer, the term of this patent is extended or adjusted under 35 U.S.C. 154(b) by 69 days.

(21) Appl. No.: 13/864,826

(22) Filed: Apr. 17, 2013

(65) Prior Publication Data

US 2013/0289617 A1  Oct. 31, 2013

Related U.S. Application Data

(63) Continuation of application No. PCT/JP2012/076594, filed on Oct. 15, 2012.

(30) Foreign Application Priority Data

Mar. 21, 2012  (JP) .................................. 2012-064497

(51) Int. Cl.
*A61B 17/00*  (2006.01)
*A61B 17/29*  (2006.01)
*A61B 10/06*  (2006.01)

(52) U.S. Cl.
CPC ........... *A61B 17/2909* (2013.01); *A61B 17/29* (2013.01); *A61B 10/06* (2013.01); *A61B 2017/2903* (2013.01); *A61B 2090/034* (2016.02)

(58) Field of Classification Search
CPC ................ A61B 17/29; A61B 17/2909; A61B 2017/292; A61B 10/06; A61B 2017/0046; A61B 17/30; A61B 2017/2927; A61B 17/221; A61B 17/282; A61B 2017/2926; A61B 2017/2825; A61B 2017/2939; A61B 2017/2903; A61B 2019/304
(Continued)

(56) References Cited

U.S. PATENT DOCUMENTS 2,252,798 A * 8/1941 Arnold ..................... A61C 3/14
433/158
5,258,005 A * 11/1993 Christian ...................... 606/205
(Continued)

FOREIGN PATENT DOCUMENTS

DE       43 00 307 A1     7/1994
EP       1985250 A2 * 10/2008 ............. A61B 18/14
(Continued)

OTHER PUBLICATIONS

Nov. 6, 2012 International Search Report issued in International Application No. PCT/JP2012/076594 (with translation).
(Continued)

*Primary Examiner* — Amy R Weisberg
(74) *Attorney, Agent, or Firm* — Oliff PLC (57) ABSTRACT

An endoscopic treatment tool includes a sheath, a support portion which is attached to a distal end of the sheath, a pair of forceps members which are provided on the support portion, a linear portion which is inserted through the sheath so that the linear portion is capable of advancing and retracting, the linear portion causing facing surfaces each provided on the pair of forceps members to approach each other, and the linear portion separating the pair of facing surfaces from each other, an engaging portion which is provided in the support portion, an engaged portion which is provided in the linear portion, and a moving mechanism that
(Continued)

moves the position of the distal end portion of the linear portion to a distal end position closer to the distal end side than the engaged portion.

8 Claims, 8 Drawing Sheets

(58) Field of Classification Search
USPC ......................................................... 606/205
See application file for complete search history.

(56) References Cited

U.S. PATENT DOCUMENTS

| | | | | |
|---|---|---|---|---|
| 5,304,203 | A * | 4/1994 | El-Mallawany et al. ..... | 606/207 |
| 5,338,317 | A * | 8/1994 | Hasson et al. ................ | 606/206 |
| 5,618,307 | A * | 4/1997 | Donlon et al. ................ | 606/205 |
| 5,626,607 | A * | 5/1997 | Malecki et al. .............. | 606/205 |
| 5,849,022 | A * | 12/1998 | Sakashita et al. ............ | 606/174 |
| 6,319,257 | B1 * | 11/2001 | Carignan et al. ............. | 606/99 |
| 6,443,909 | B1 * | 9/2002 | Ouchi ............................ | 600/562 |
| 6,569,105 | B1 * | 5/2003 | Kortenbach et al. ......... | 600/562 |
| 8,142,473 | B2 * | 3/2012 | Cunningham ................ | 606/205 |
| 8,162,973 | B2 * | 4/2012 | Cunningham ................ | 606/205 |
| 8,317,820 | B2 * | 11/2012 | Surti .............................. | 606/205 |
| 8,377,044 | B2 * | 2/2013 | Coe et al. ...................... | 606/1 |
| 8,568,443 | B1 * | 10/2013 | Jackman et al. .............. | 606/205 |
| 8,568,444 | B2 * | 10/2013 | Cunningham ................ | 606/205 |
| 8,974,492 | B2 * | 3/2015 | Suzuki .................. | A61B 17/29 |
| | | | | 600/104 |
| 2001/0007057 | A1 * | 7/2001 | Lippitt et al. ................. | 600/564 |
| 2002/0151890 | A1 * | 10/2002 | Scholer et al. ................ | 606/48 |
| 2003/0097147 | A1 * | 5/2003 | Prestel .......................... | 606/205 |
| 2003/0195432 | A1 * | 10/2003 | Kortenbach et al. ......... | 600/562 |
| 2004/0181169 | A1 * | 9/2004 | Diamond et al. ............. | 600/564 |
| 2005/0187547 | A1 * | 8/2005 | Sugi ............................... | 606/48 |
| 2007/0073185 | A1 * | 3/2007 | Nakao ........................... | 600/564 |
| 2008/0140091 | A1 * | 6/2008 | DeDeyne et al. ............. | 606/144 |
| 2010/0042140 | A1 * | 2/2010 | Cunningham ................ | 606/205 |
| 2011/0040322 | A1 * | 2/2011 | Major ............................ | 606/206 |
| 2012/0089176 | A1 * | 4/2012 | Sigmon et al. ................ | 606/205 |

FOREIGN PATENT DOCUMENTS

| | | |
|---|---|---|
| JP | B2-4056989 | 3/2008 |
| JP | B2-4197983 | 12/2008 |
| WO | WO 2012/002091 A1 | 1/2012 |

OTHER PUBLICATIONS

Dec. 2, 2014 Search Report issued in European Patent Application No. 12867726.7.

* cited by examiner

ENDOSCOPE TREATMENT TOOL

This application claims priority of and the benefit of Japanese Patent Application No. 2012-064497 filed on Mar. 21, 2012, and is a continuous application of international application PCT/JP2012/076594 filed on Oct. 15, 2012, the disclosures thereof are incorporated herein by reference.

BACKGROUND OF THE INVENTION

Field of the Invention

The present invention relates to an endoscopic treatment tool that is used by being endoscopically inserted into a body cavity.

Description of Related Art

In the related art, endoscopic treatment tools (hereinafter, simply referred to as "treatment tools") used for performing various treatments on tissues in the body cavity by being endoscopically inserted into the body cavity have been considered. As an example of the treatment tools, treatment tools described in Japanese Patent Nos. 4197983 and 4056989 have been known.

A pair of forceps members supported relatively and rotatably around a rotation axis is provided on a distal end of the treatment tool.

The rotation axis is provided to a distal end portion of a sheath that has a long shape, and a manipulation wire (linear portion) is inserted through the sheath so that the wire can advance and retreat. A manipulation portion is connected to the proximal ends of the sheath and the manipulation wire. Link members are each attached to the proximal ends of the pair of forceps members. The proximal ends of the link members are rotatably connected to the distal end of the manipulation wire.

The pair of forceps members are relatively rotated around the rotation axis by manipulating the manipulation portion and causing the manipulation wire to advance or retreat with respect to the sheath, and thus the forceps members can be switched between a closed state in which the pair of forceps members come into contact with each other and a fully open state in which the pair of forceps members are separated from each other.

SUMMARY OF THE INVENTION

According to a first aspect of the present invention, an endoscopic treatment tool includes a sheath; a support portion which is attached to a distal end side of the sheath; a pair of forceps members placed ahead of the sheath and supported to be rotatable relatively around a rotation axis provided on the support portion; a linear portion which is inserted through the sheath so that the linear portion is capable of advancing and retracting, the linear portion causing facing surfaces each provided on the distal end side rather than the rotation axis in the pair of forceps members to approach each other as a distal end portion of the linear portion is separated from the rotation axis, and the linear portion separating the pair of facing surfaces from each other as the distal end portion of the linear portion approaches to the rotation axis; an engaging portion which is provided between the distal end portion of the sheath and the rotation axis in the support portion; an engaged portion which is provided on a position closer to a proximal end side than the distal end portion in the linear portion, and is engaged to the engaging portion when the linear portion moves toward the distal end side; and a moving mechanism which moves the position of the distal end portion of the linear portion with respect to the engaged portion to a distal end position closer to the distal end side than the engaged portion in a longitudinal direction of the sheath. The pair of facing surfaces are separated from each other by moving the distal end portion of the linear portion to the distal end position by the moving mechanism in the state in which the engaged portion is engaged to the engaging portion.

According to a second aspect of the present invention, in the endoscopic treatment tool related to the first aspect, the moving mechanism may move the position of the distal end portion of the linear portion with respect to the engaged portion from a reference position to a distal end position closer to a distal end side than the reference position. The pair of facing surfaces are separated from each other relative to a position of the time at which the distal end portion of the linear portion is at the reference position, by engaging the engaged portion to the engaging portion in the state in which the distal end portion of the linear portion is placed at the reference position, and moving the distal end portion of the linear portion to the distal end position by the moving mechanism.

According to a third aspect of the present invention, in the endoscopic treatment tool related to the second aspect, the linear portion may have a distal end side linear member which forms the distal end portion of the linear portion, a distal end side thereof connected to at least one of the pair of forceps members, and a proximal end side thereof connected to the engaged portion, and a proximal end side linear member which is placed at a position closer to the proximal end side than the distal end side linear member, a distal end side thereof fixed to the engaged portion. The moving mechanism may have a male screw portion which is formed in one of the proximal end side of the distal end side linear member and the engaged portion, and sets an axial line of the distal end side linear member as a spiral axis, and a female screw portion which is formed in the other of the proximal end side of the distal end side linear member and the engaged portion and is threadedly engaged with the male screw portion. The position of the distal end side linear member with respect to the engaged portion may be switched between the reference position and the distal end position in the longitudinal direction, by adjusting the length by which the male screw portion and the female screw portion are threadedly engaged with each other.

According to a fourth aspect of the present invention, the endoscopic treatment tool related to the third aspect may further include a first link member, a distal end side thereof rotatably connected to a portion closer to the proximal end side than the rotation axis of one of the pair of forceps members, a second link member, a distal end side thereof rotatably connected to a portion of the proximal end side rather than the rotation axis of the other of the pair of forceps members, and a second rotation axis which rotatably connects the proximal end side of the first link member and the proximal end side of the second link member. The distal end side linear member may be connected to the second rotation axis. A length from a contact surface of the engaged portion which comes into contact with the engaging portion when the engaged portion is engaged to the engaging portion to the second rotation axis may be lengthened, as the length in which the male screw portion and the female screw portion are threadedly engaged with each other is shortened.

According to a fifth aspect of the present invention, in the endoscope treatment tool related to the second aspect, a through hole which penetrates in the longitudinal direction and through which the linear portion is inserted so that linear portion is able to advance and retract may be formed in the engaged portion. The moving mechanism may have a concave portion which is formed on one of an outer circumferential surface of the linear portion and an inner circumferential surface of the through hole, and a convex portion which is formed on the other of the outer circumferential surface of the linear portion and the inner circumferential surface of the through hole and engaged with the concave portion, the convex portion elastically deformed so that the engagement with the concave portion is released when the engaged portion and the linear portion receive a force of a certain level or more relatively in the longitudinal direction, and comes into slidably contacts with the one thereof. A position of the distal end portion of the linear portion with respect to the engaged portion when the concave portion is engaged with the convex portion may become the reference position, and a position of the distal end portion of the linear portion with respect to the engaged portion when the engagement between the concave portion and the convex portion is released and the distal end portion of the linear portion moves toward the distal end side with respect to the engaged portion may become the distal end position.

According to a sixth aspect of the present invention, in the endoscopic treatment tool related to the fifth aspect, a support member which extends to the proximal end side may be provided on the engaged portion.

According to a seventh aspect of the present invention, the endoscopic treatment tool related to the fifth aspect of the present invention may further include a first link member, a distal end side thereof rotatably connected to a portion closer to a proximal end side than the rotation axis of one of the pair of forceps members, a second link member, a distal end side thereof rotatably connected to a portion closer to a proximal end side than the rotation axis of the other of the pair of forceps members, and a second rotation axis which rotatably connects the proximal end side of the first link member and the proximal end side of the second link member. The distal end portion of the linear portion may be connected to the second rotation axis. The length from the contact surface, in the engaged portion, coming into contact with the engaging portion to the second rotation axis when the engaged portion is engaged to the engaging portion may be lengthened, as the distal end portion of the linear portion moves toward the distal end side.

DETAILED DESCRIPTION OF THE INVENTION

First Embodiment

Hereinafter, an endoscopic treatment tool related to the first embodiment of the present invention will be described with reference to FIGS. 1 to 5. Hereinafter, a case in which the endoscopic treatment tool is a grasping forceps will be described as an example.

Figure 1:
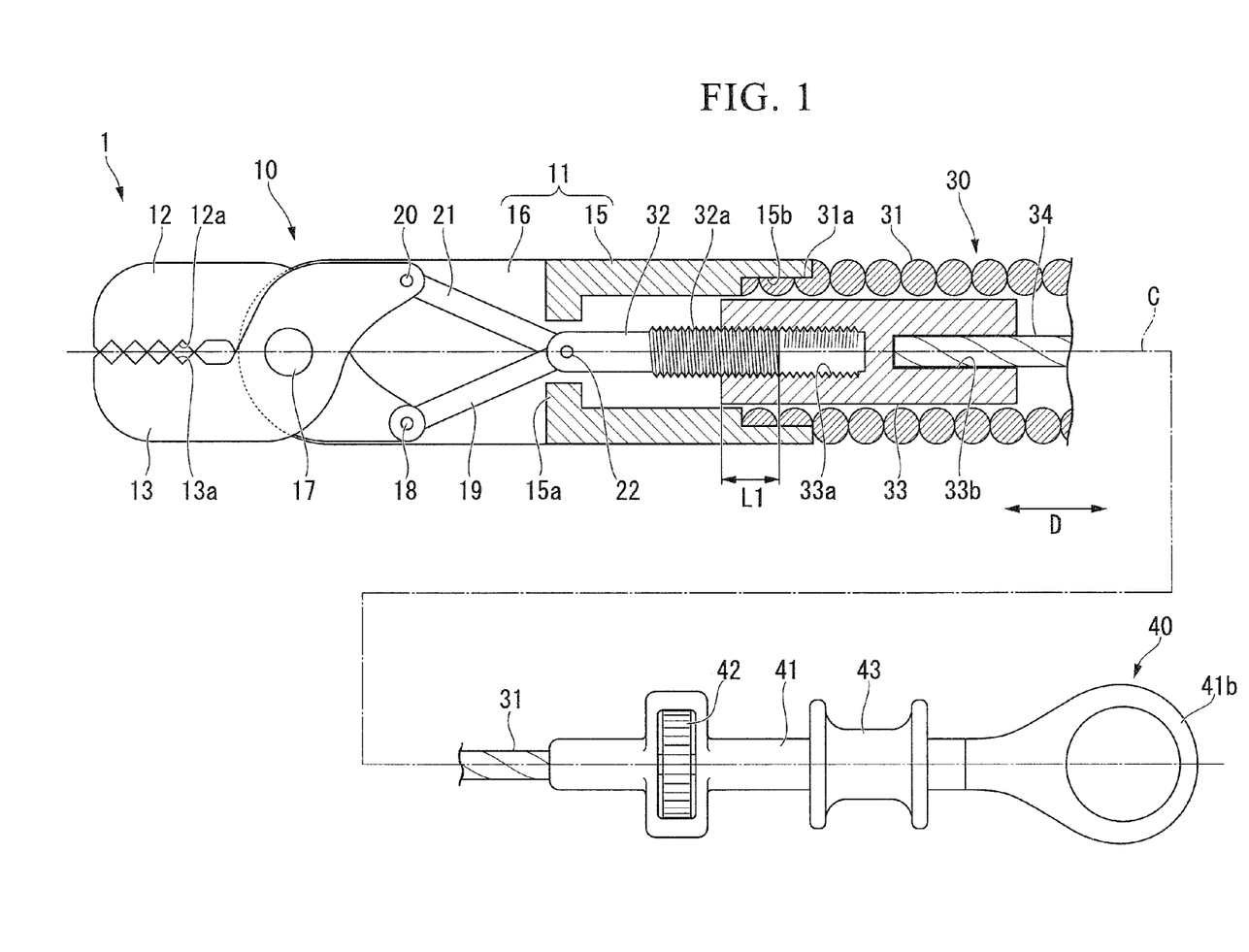
FIG. 1 is a view of a side surface in a closed state of grasping forceps related to a first embodiment of the present invention, a portion of which is broken.

As shown in FIG. 1, a grasping forceps 1 includes a grasping portion 10 that grasps a tissue, an insertion portion 30 having flexibility that is provided at a proximal end side of the grasping portion 10, and a manipulation portion 40 that is provided at the proximal end side of the insertion portion 30 and manipulates the grasping portion 10.

The grasping portion 10 includes a distal end cover member (support portion) 11, and a pair of forceps members 12 and 13 that are rotatably supported by the distal end cover member 11.

The distal end cover member 11 has a cylindrical portion 15 having a cylindrical shape in which an axial line C extends back and forth, and a pair of covers 16 that extend such that the axial line C is interposed therebetween from the distal end surface of the cylindrical portion 15 (one of the covers 16 is not shown).

In the distal end portion of the cylindrical portion 15, an annular engaging portion 15a protruding from an inner circumferential surface is provided. In the proximal end portion of the cylindrical portion 15, a stepped portion 15b in which an inner diameter thereof is set to be greater than other portions of the cylindrical portion 15 is formed.

In the distal end portions of the pair of covers 16, a rotation axis 17 that joins the covers 16 is provided.

When viewed from the side surface, the forceps members 12 and 13 are placed so as to intersect with each other in a central portion of the extension direction. Each of the forceps members 12 and 13 is rotatably supported around the above-mentioned rotation axis 17 in the central portion.

In this example, facing surfaces in the distal end portions of the forceps members 12 and 13 are anti-slip surfaces 12a and 13a formed with minute concaves and convexes. The forceps members 12 and 13 are placed between the pair of covers 16. The placement of the forceps members 12 and 13 can be switched between a closed state in which the anti-slip surfaces 12a and 13a come into contact with each other, and a fully open state in which the anti-slip surfaces 12a and 13a are separated from each other until the stopper 33 is engaged to an engaging portion 15a to be described below of the distal end cover member 11.

That is, the forceps members 12 and 13 rotate around the rotation axis 17, whereby an opening angle of the anti-slip surfaces 12a and 13a can be adjusted.

The distal end cover member 11 and the forceps members 12 and 13 are formed of a metal having biocompatibility such as stainless steel.

A distal end of a link member (a first link member) 19 is rotatably connected to the proximal end of the forceps member 12 via a link rotation axis 18. Similarly, a distal end of a link member (a second link member) 21 is rotatably connected to the proximal end of the forceps member 13 via a link rotation axis 20. The proximal end of the link member 19 and the proximal end of the link member 21 are rotatably connected to each other by a common rotation axis (second rotation axis) 22. The common rotation axis 22 is provided closer to the proximal end sides than the forceps members 12 and 13 and is placed on the axial line C.

The forceps members 12 and 13, the link members 19 and 21, and the rotation axes 18, 20 and 22 configured in this manner form a well-known pantograph type link mechanism. That is, as the common rotation axis 22 moves toward the proximal end side, the forceps members 12 and 13 rotate around the rotation axis 17. Thus, the forceps members 12 and 13 approach each other, and the closed state in which the opening angle is 0 is obtained. Meanwhile, as the common rotation axis 22 moves toward the distal end side, the anti-slip surfaces 12a and 13a are separated from each other, and the fully open state in which the opening angle is maximum is obtained.

The insertion portion 30 has a sheath 31, a wire connection portion (a distal end side linear member) 32, a stopper (an engaged portion) 33, and a manipulation wire (a proximal end side linear member) 34. The wire connection portion 32 is inserted through the sheath 31 in the state in which the distal end is connected to the common rotation axis 22. A stopper 33 is connected to the proximal end of the wire connection portion 32. The manipulation wire 34 is fixed to the proximal end of the stopper 33. The wire connection portion 32 and the manipulation wire 34 form a linear portion.

As the sheath 31, a coil sheath closely wound in a longitudinal direction D of the sheath 31 is used. The sheath 31 has flexibility, and has compressive resistance in the longitudinal direction D.

A stepped portion 31a is formed on the outer circumferential surface of the distal end of the sheath 31. By performing the laser welding, or the like, between the stepped portion 31a and the stepped portion 15b in the state of engaging the stepped portion 31a of the sheath 31 with the stepped portion 15b of the distal end cover member 11, the sheath 31 is attached to the proximal end portion of the distal end cover member 11.

By attaching the distal end cover member 11 and the sheath 31 in this manner, the outer diameters of the distal end cover member 11 and the sheath 31 can set to be equal to each other, and it is possible to improve the insertability of the grasping portion 10 and the insertion portion 30.

A coating tube having the low frictional resistance may be provided on the outer circumferential surface of the sheath 31.

The wire connection portion 32 is formed in a rod shape and is placed on the axial line C. A male screw portion 32a is formed on the outer circumferential surface of the proximal end of the wire connection portion 32.

The stopper 33 is formed in an approximately cylindrical shape extending in the longitudinal direction D. On a distal end surface (contact surface) 33c of the stopper 33, a hole portion extending in the longitudinal direction D is formed. On the inner circumferential surface of the hole portion, a female screw portion 33a threadedly engaged with the male screw portion 32a is formed. The male screw portion 32a and the female screw portion 33a form a moving mechanism. The male screw portion 32a and the female screw portion 33a are formed so that spiral axes of each screw coincide with the axial line C.

Since the wire connection portion 32 is connected to the rotation axis 17 via the link members 19 and 21 and the forceps members 12 and 13, the wire connection portion 32 does not rotate around the axial line C with respect to the distal end cover member 11. A length of which the male screw portion 32a and the female screw portion 33a are threadedly engaged with each other is changed by rotating the stopper 33 around the axial line C with respect to the wire connection portion 32, and it is possible to move the position of the wire connection portion 32 with respect to the stopper 33 in the longitudinal direction D. In FIG. 1, a length L1 in the longitudinal direction D of which the male screw portion 32a is threadedly engaged with the female screw portion 33a is set to be smaller than the entire length of the female screw portion 33a. For this reason, the position of the wire connection portion 32 with respect to the stopper 33 becomes a distal end position in which the wire connection portion 32 moves toward the distal end side.

On the proximal end surface of the stopper 33, a hole portion 33b extending in the longitudinal direction D is formed.

The distal end of the manipulation wire 34 is fixed to the hole portion 33b of the stopper 33. The proximal end of the manipulation wire 34 extends up to a manipulation portion 40. The stopper 33 and the manipulation wire 34 are placed on the axial line C.

The wire connection portion 32, the stopper 33, and the manipulation wire 34 are inserted through the cylindrical portion 15 of the distal end cover member 11 and the sheath 31 so that they can advance and retract. A through hole formed in the above-mentioned engaging portion 15a is formed so that the wire connection portion 32 and the link members 19 and 21 can be inserted into the through hole. An outer diameter of the stopper 33 is set to be greater than an inner diameter of the through hole of the engaging portion 15a, and the distal end surface 33c of the stopper 33 is engaged to the engaging portion 15a.

The wire connection portion 32, the stopper 33, and the manipulation wire 34 are preferably formed of a metal having biocompatibility such as stainless steel.

The manipulation portion 40 has a manipulation portion main body 41 connected to the proximal end portion of the sheath 31, a rotary handle 42 placed so as to cover an intermediate portion of the manipulation wire 34 in the longitudinal direction D, and a slider 43 attached to the proximal end portion of the manipulation wire 34.

Figure 2:
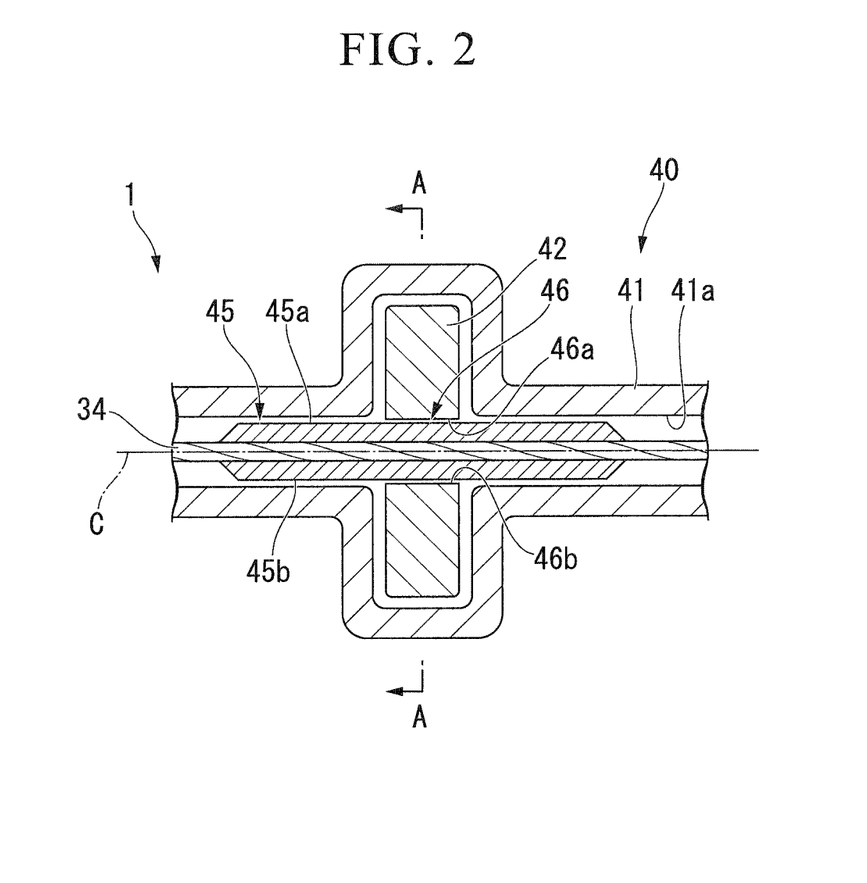
FIG. 2 is a cross-sectional view of a side surface in major parts of the grasping forceps related to the first embodiment of the present invention.
Figure 3:
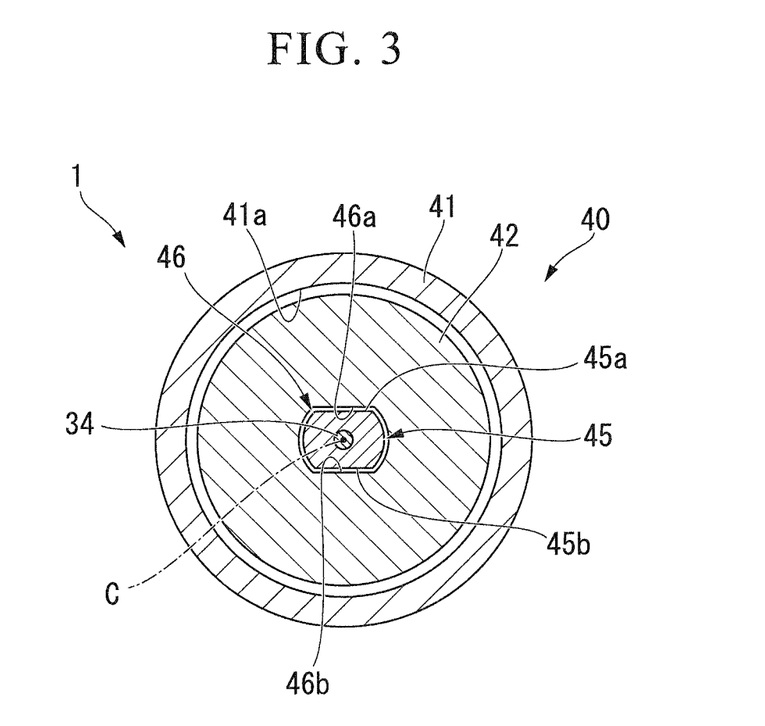
FIG. 3 is a cross-sectional view taken along cutting line A-A in FIG. 2.

As shown in FIGS. 2 and 3, the manipulation portion main body 41 is formed in an approximately cylindrical shape. On the outer surface of the manipulation portion main body 41, a slit (not shown) communicating with a pipeline 41a of the manipulation portion main body 41 is formed. A finger-hanging ring 41b is provided in the proximal end portion of the manipulation portion main body 41 (see FIG. 1).

A transformed pipe 45 is fixed onto the outer circumferential surface of the intermediate portion of the manipulation wire 34 in the longitudinal direction D.

Engaging planes 45a and 45b, which are parallel to the axial line C and placed so as to be parallel to each other with the manipulation wire 34 interposed therebetween, are formed on the outer surface of the transformed pipe 45.

The rotary handle 42 is formed in a disk shape. In the central portion of the rotary handle 42, an insertion hole 46 penetrating in a thickness direction is formed. On the inner circumferential surface of the insertion hole 46, facing planes 46a and 46b parallel to the thickness direction of the rotary handle 42 and facing each other are formed.

The rotary handle 42 is supported by the manipulation portion main body 41 so that a part thereof is exposed from the manipulation portion main body 41.

The transformed pipe 45 is inserted through the insertion hole 46 of the rotary handle 42. Small gaps are provided between the facing plane 46a of the insertion hole 46 and the engaging plane 45a of the transformed pipe 45, and between the facing plane 46b of the insertion hole 46 and the engaging plane 45b of the transformed pipe 45.

The rotary handle 42 and the transformed pipe 45 configured in this manner are configured so that the transformed pipe 45 can advance and retract in the longitudinal direction D with respect to the insertion hole 46 of the rotary handle 42. Meanwhile, when the rotary handle 42 is rotated around the axial line C, the facing plane 46a is engaged to the engaging plane 45a, and the facing plane 46b is engaged to the engaging plane 45b. Thus, it is possible to rotate the manipulation wire 34 with the transformed pipe 45 fixed thereto around the axial line C.

As shown in FIG. 1, the slider 43 is provided on the outer circumferential surface between the rotary handle 42 and the finger-hanging ring 41b in the manipulation portion main body 41 so that the slider 43 can advance and retract in the longitudinal direction D. The slider 43 is attached to the proximal end portion of the manipulation wire 34 through the above-mentioned slit of the manipulation portion main body 41.

In the closed state (first form) shown in FIG. 1 of the grasping forceps 1 of the present embodiment, only the portion of the proximal end side of the male screw portion 32a of the wire connection portion 32 is threadedly engaged with the female screw portion 33a of the stopper 33. At this time, the position of the wire connection portion 32 with respect to the stopper 33 becomes the distal end position. That is, the range in which the male screw portion 32a and the female screw portion 33a are threadedly engaged with each other is narrowly set. Moreover, by moving the common rotation axis 22 toward the proximal end side via the manipulation wire 34 by the slider 43, the anti-slip surfaces 12a and 13a of the forceps members 12 and 13 enter the closed state in which the surfaces come into contact with each other.

Next, the operation of the grasping forceps 1 configured in this manner will be described.

First, the description will be given of a case in which the grasping portion 10 and the insertion portion 30 of the grasping forceps 1 of the present embodiment are inserted into a living body or the like and used in an environment in which there is relatively sufficient space in a periphery.

Figure 4:
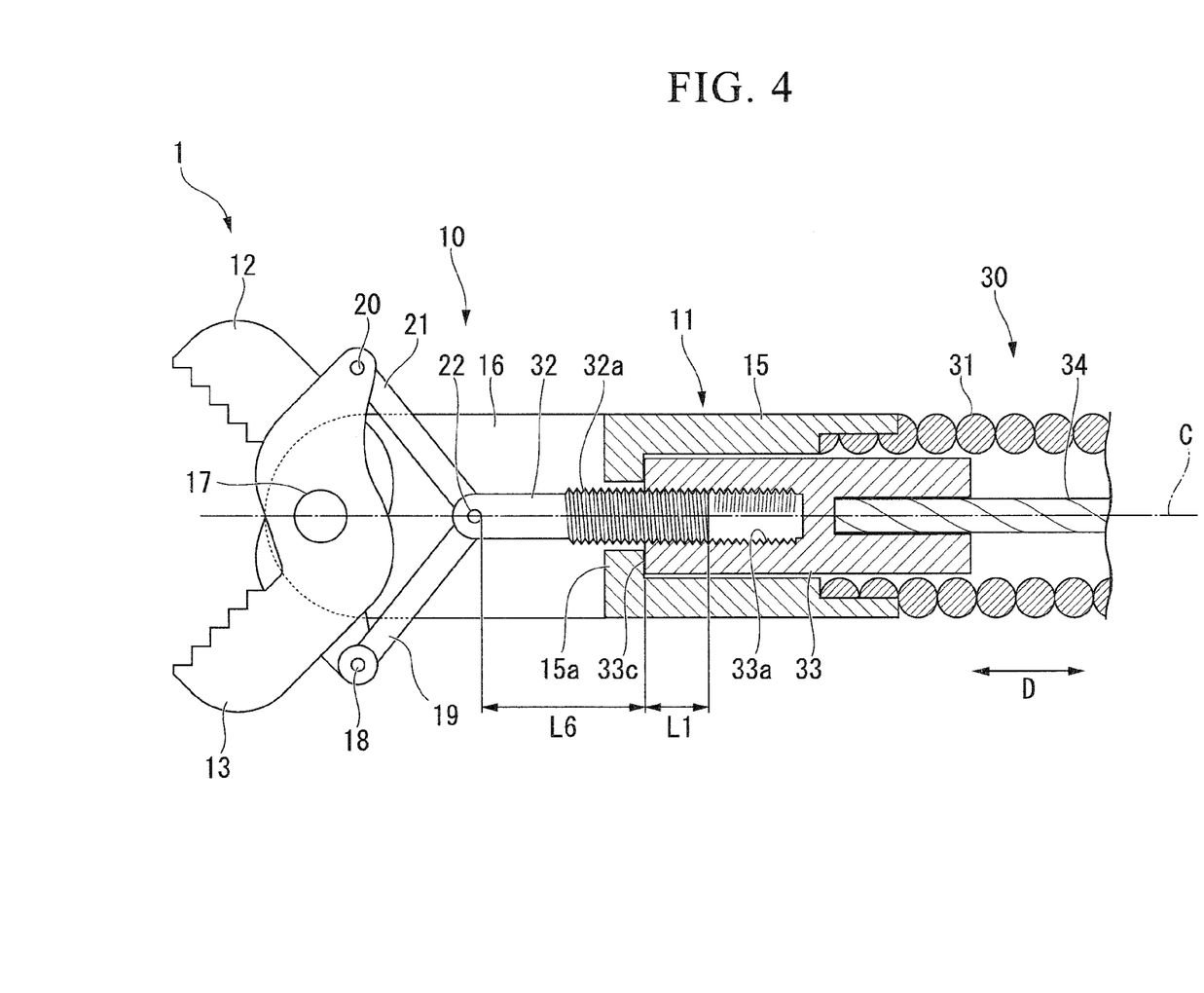
FIG. 4 is a cross-sectional view of a side surface of a distal end side in a fully open state of the grasping forceps related to the first embodiment of the present invention.

An operator inserts a thumb into the finger-hanging ring 41b of the grasping forceps 1 of the closed state, hangs a forefinger and a middle finger on the concave portion of the slider 43, and supports the grasping forceps 1. The operator inserts the grasping portion 10 into the living body. The operator presses the slider 43 into the manipulation portion main body 41 when the grasping portion 10 reaches the vicinity of the tissue to be treated. Moreover, as shown in FIG. 4, the operator brings the distal end surface 33c of the stopper 33 into contact with the engaging portion 15a of the distal end cover member 11. At this time, the forceps members 12 and 13 rotate around the rotation axis 17 and enter the fully open state, and the grasping forceps 1 is in the fully open state (second form).

The operator brings the anti-slip surfaces 12a and 13a into contact with the tissue. The operator returns the grasping forceps 1 to the closed state by pulling the slider 43 with respect to the manipulation portion main body 41 (when the tissue interposed between the anti-slip surfaces 12a and 13a is thick, in some cases, the grasping forceps 1 does not return to the closed state), grasps the tissue between the forceps members 12 and 13, and performs the suitable treatment.

Next, the description will be given of a case in which the grasping forceps 1 is used in an environment such as inside of an esophagus in which there is relatively insufficient space in the periphery.

Figure 5:
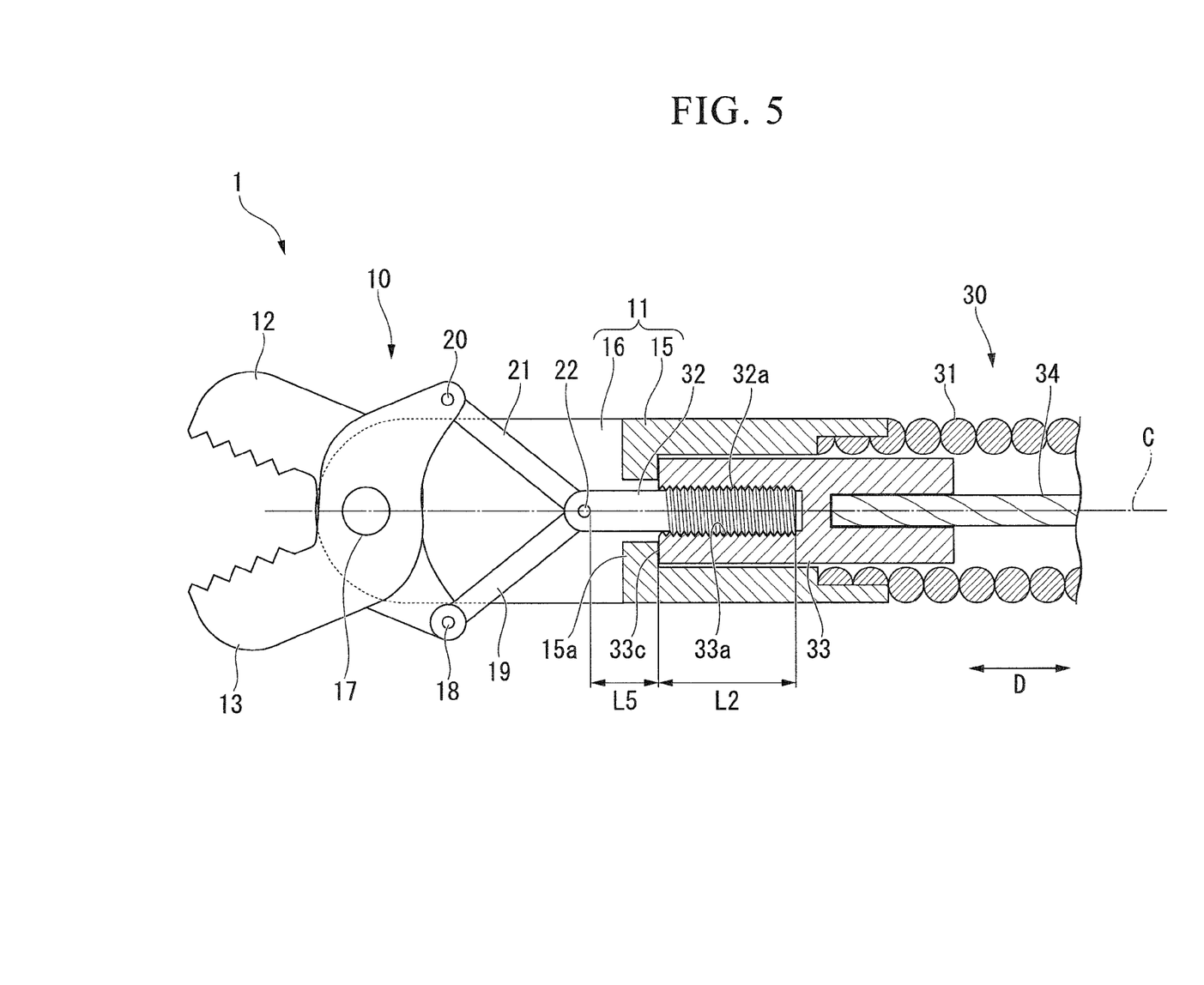
FIG. 5 is a cross-sectional view of a side surface of a distal end side in a half-open state of the grasping forceps related to the first embodiment of the present invention.

The operator rotates the stopper 33 with respect to the wire connection portion 32 by rotating the rotary handle 42 around the axial line C. Moreover, the operator threadedly engages the male screw portion 32a of the wire connection portion 32 with the inner side of the female screw portion 33a of the stopper 33. That is, as shown in FIG. 5, a length L2 of which the male screw portion 32a and the female screw portion 33a are threadedly engaged with each other is set to be longer than the above-mentioned length L1 of the distal end position. By such an operation, the position of the wire connection portion 32 with respect to the stopper 33 becomes the reference position in which the wire connection portion 32 moves from the above-mentioned distal end position to the proximal end side.

The operator presses the slider 43 in this state. Moreover, the operator brings the distal end surface 33c of the stopper 33 into contact with the engaging portion 15a of the distal end cover member 11, and sets the grasping forceps 1 to a half-open state (third form). At this time, since the wire connection portion 32 is located at the reference position, the length of which the wire connection portion 32 protrudes to the distal end side with respect to the stopper 33 becomes shorter than that of the fully open state in which the wire connection portion 32 shown in FIG. 4 is located at the distal end position. For this reason, the anti-slip surfaces 12a and 13a enter a half-open state in which the opening angle is between the closed state and the fully open state.

Even when the slider 43 is pressed to bring the stopper 33 into contact with the engaging portion 15a by allowing the slider 43 to advance and retract while the wire connection portion 32 is placed at the reference position, the anti-slip surfaces 12a and 13a are opened only in the half-open state. If the length L2 by which the male screw portion 32a and the female screw portion 33a are threadedly engaged with each other is a constant value, the opening angle of the anti-slip surfaces 12a and 13a becomes a constant value when the slider 43 is pressed and enters the half-open state. For this reason, the forceps members 12 and 13 are suppressed from coming into contact with the peripheral tissue, and the operator can effectively perform the surgery.

In this manner, by adjusting the length by which the male screw portion 32a and the female screw portion 33a are threadedly engaged with each other, it is possible to switch the position of the wire connection portion 32 with respect to the stopper 33 between the reference position and the distal end position in the longitudinal direction D.

Furthermore, the grasping forceps 1 of the present embodiment is shifted from the half-open state to the fully open state by rotating the rotary handle 42 around the axial line C and moving the wire connection portion 32 to the distal end position while bringing the stopper 33 into contact with the engaging portion 15a. When the grasping forceps 1 is shifted from the half-open state to the fully open state, the anti-slip surfaces 12a and 13a are separated from each other, and the opening angle becomes larger.

Furthermore, in the longitudinal direction D, the length from the distal end surface 3c of the stopper 33 to the common rotation axis 22 is a length L5 in the half-open state of FIG. 5. In contrast, as the length L2 by which the male screw portion 32a and the female screw portion 33a are threadedly engaged with each other is set to be shorter like the screwing length L1 in the fully open state of FIG. 4, the length from the distal end surface 33c to the common rotation axis 22 becomes longer like the length L6.

That is, in the case of the present embodiment, when the distal end surface 33c of the stopper 33 is brought into contact with the engaging portion 15a, the sum of the length by which the male screw portion 32a and the female screw portion 33a are threadedly engaged with each other and the length from the distal end surface 33c to the common rotation axis 22 is constant. For this reason, as one length becomes longer, the other length becomes smaller. Specifically, as the length by which the male screw portion 32a and the female screw portion 33a are threadedly engaged with each other becomes shorter, the length from the distal end surface 33c to the common rotation axis 22 becomes longer. The opening angle of the anti-slip surfaces 12a and 13a increases along with this.

As described above, according to the grasping forceps 1 of the present embodiment, by adjusting the position in the longitudinal direction D of the wire connection portion 32 with respect to the stopper 33 to the reference position and the distal end position using the moving mechanism, when the stopper 33 is engaged to the engaging portion 15a, the separated state of the anti-slip surfaces 12a and 13a can be adjusted to the half-open state and the fully open state. If the length by which the male screw portion 32a and the female screw portion 33a are threadedly engaged with each other is constant, the opening angle of the anti-slip surfaces 12a and 13a is constant when the stopper 33 is engaged to the engaging portion 15a.

Thus, it is possible to easily adjust the anti-slip surfaces 12a and 13a, that is, the forceps members 12 and 13, from the fully open state to the half-open state in which the opening angle of the anti-slip surfaces 12a and 13a becomes the constant value, using the moving mechanism. Furthermore, by shifting from the half-open state to the fully-open state using the moving mechanism, it is possible to further separate the anti-slip surfaces 12a and 13a separated from each other.

Furthermore, the moving mechanism is constituted by the male screw portion 32a of the wire connection portion 32 and the female screw portion 33a of the stopper 33. For this reason, the length by which the male screw portion 32a and the female screw portion 33a are threadedly engaged with each other, that is, the opening angle of the anti-slip surfaces 12a and 13a when pressing the slider 43, can be continuously set, and the moving mechanism can be cheaply formed.

In addition, in the present embodiment, the male screw portion 32a is formed in the proximal end of the wire connection portion 32, and the female screw portion 33a is formed in the distal end of the stopper 33. However, the female screw portion may be formed in the proximal end of the wire connection portion 32, and the male screw portion threadedly engaged with the female screw portion may be formed in the distal end of the stopper 33.

Second Embodiment

Next, an endoscopic treatment tool related to the second embodiment of the present invention will be described with reference to FIGS. 6 to 8. In addition, the same parts as those of the first embodiment are denoted by the same reference numerals, a description thereof will be omitted here, and only different points will be described.

Figure 6:
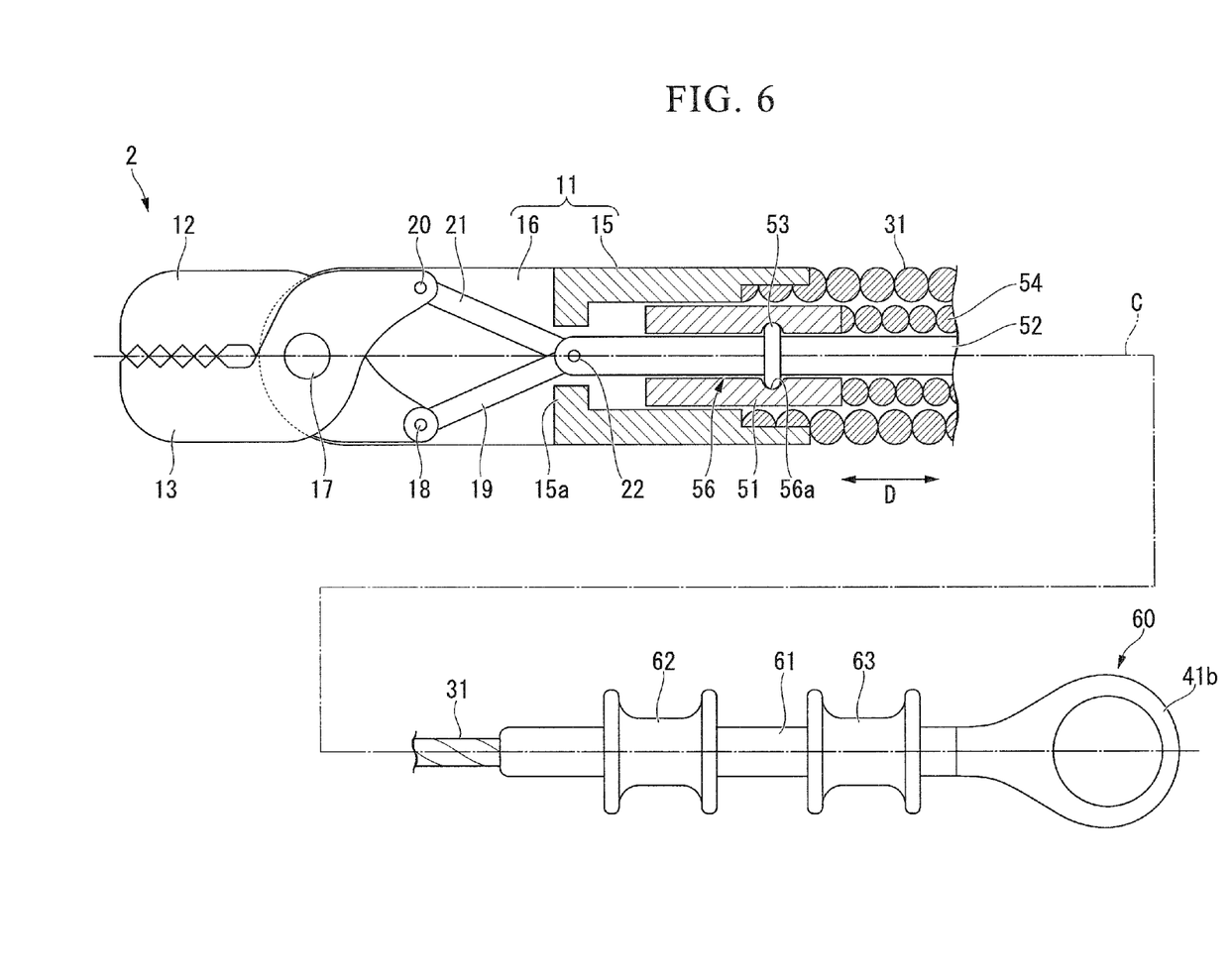
FIG. 6 is a view of the side surface in the closed state of the grasping forceps related to the second embodiment of the present invention, a portion of which is broken.

As shown in FIG. 6, a grasping forceps 2 of the present embodiment includes a stopper 51, a manipulation wire (linear portion) 52, an O ring (convex portion) 53, an inner sheath (support member) 54, and a manipulation portion 60, instead of the wire connection portion 32, the stopper 33, the manipulation wire 34, and the manipulation portion 40 of the grasping forceps 1 of the first embodiment.

The stopper 51 is formed in an approximately cylindrical shape. On the inner circumferential surface of a through hole 56 penetrating in the longitudinal direction D in the stopper 51, a concave portion 56a is formed throughout the entire circumference.

The above-mentioned O ring 53 formed of an elastic material such as rubber is attached to the outer circumferential surface of the manipulation wire 52. The O ring 53 is constituted so as to protrude from the outer circumferential surface of the manipulation wire 52. The outer diameter of the O ring 53 is set to be slightly greater than the inner diameter of the through hole 56 of the stopper 51, and set to be slightly smaller than the inner diameter of the concave portion 56a. The O ring 53 and the concave portion 56a of the stopper 51 form the moving mechanism.

In the stopper 51 and the O ring 53 configured in this manner, when the manipulation wire 52 is inserted through the through hole 56 of the stopper 51, the O ring 53 is engaged with the concave portion 56a. Furthermore, when the O ring 53 comes into contact with the inner circumferential surface of the through hole 56 other than the concave portion 56a, the O ring 53 is elastically deformed so as to be crushed.

The distal end of the manipulation wire 52 is connected to the common rotation axis 22.

The inner sheath 54 is formed of the same material as that of the sheath 31, and inserted through the sheath 31 so that the inner sheath 54 can advance and retract. The distal end of the inner sheath 54 is attached to the proximal end surface of the stopper 51. The proximal end of the inner sheath 54 extends to the manipulation portion 60.

The manipulation portion 60 has a manipulation portion main body 61 connected to the proximal end portion of the sheath 31, a sheath slider 62 attached to the proximal end portion of the inner sheath 54, and a wire slider 63 attached to the proximal end portion of the manipulation wire 52.

The manipulation portion main body 61 is formed in an approximately cylindrical shape. On the outer surface of the manipulation portion main body 61, a first slit and a second slit (not shown) communicating with the pipeline of the manipulation portion main body 61 are formed.

The sheath slider 62 is provided on the outer circumferential surface of the manipulation portion main body 61 so that the sheath slider 62 can advance and retract in the longitudinal direction D. The sheath slider 62 is attached to the proximal end portion of the inner sheath 54 through the above-mentioned first slit of the manipulation portion main body 61.

The wire slider 63 is provided on the outer circumferential surface of the manipulation portion main body 61 and closer to the proximal end side than the sheath slider 62 so that the wire slider 63 can advance and retract in the longitudinal direction D. The wire slider 63 is attached to the proximal end portion of the manipulation wire 52 through the above-mentioned second slit of the manipulation portion main body 61.

In the closed state of the grasping forceps 2 of the present embodiment shown in FIG. 6, the O ring 53 is engaged with the concave portion 56a of the stopper 51. The position of the manipulation wire 52 with respect to the stopper 51 at this time becomes the reference position. Moreover, by moving the common rotation axis 22 toward the proximal end side via the manipulation wire 52 using the wire slider 63, the anti-slip surfaces 12*a* and 13*a* of the forceps members 12 and 13 enter the closed state in which the surfaces come into contact with each other. At this time, the inner sheath 54 and the sheath slider 62 move toward the proximal end side via the stopper 51 engaged with the O ring 53.

Next, the operation of the grasping forceps 2 configured in this manner will be described.

When the grasping forceps 2 of the present embodiment is used in an environment in which there is relatively insufficient space in a periphery, an operator inserts a thumb through the finger-hanging ring 41*b* of the grasping forceps 2 of the closed state, hangs a forefinger and a middle finger on the concave portion of the wire slider 63, and supports the grasping forceps 2.

The operator inserts the grasping portion 10 into the living body. The operator presses the wire slider 63 into the manipulation portion main body 61 when the grasping portion 10 reaches the vicinity of the tissue to be treated. Moreover, as shown in FIG. 7, the operator brings the distal end surface 33*c* of the stopper 51 into contact with the engaging portion 15*a* of the distal end cover member 11. At this time, the forceps members 12 and 13 rotate around the rotation axis 17 and enter the half-open state in which the anti-slip surfaces 12*a* and 13*a* are separated from each other, and the grasping forceps 2 is in the half-open state. Since the O ring 53 is engaged with the concave portion 56*a* of the stopper 51, the opening angle of the anti-slip surfaces 12*a* and 13*a* becomes a constant value when the distal end surface 33*c* of the stopper 51 is brought into contact with the engaging portion 15*a*. Furthermore, the wire slider 63 and the sheath slider 62 also move to the distal end side.

The operator brings the anti-slip surfaces 12*a* and 13*a* into contact with the tissue. The operator returns the grasping forceps 2 to the closed state by pulling the wire slider 63 with respect to the manipulation portion main body 61, grasps the tissue between the anti-slip surfaces 12*a* and 13*a*, and performs the suitable treatment.

Next, the description will be given of a case in which the grasping forceps 2 is used in an environment in which there is relatively sufficient space in the periphery.

As described above, the operator presses the wire slider 63, shifts the wire slider 63 from the closed state to the half-open state, and then further presses the wire slider 63 to the distal end side by force of a certain level or more. In this case, the force of the certain level or more refers to a force that deforms the outer diameter of the O ring 53 to equal or less than the inner diameter of the stopper 51 as will be described later.

Figure 8:
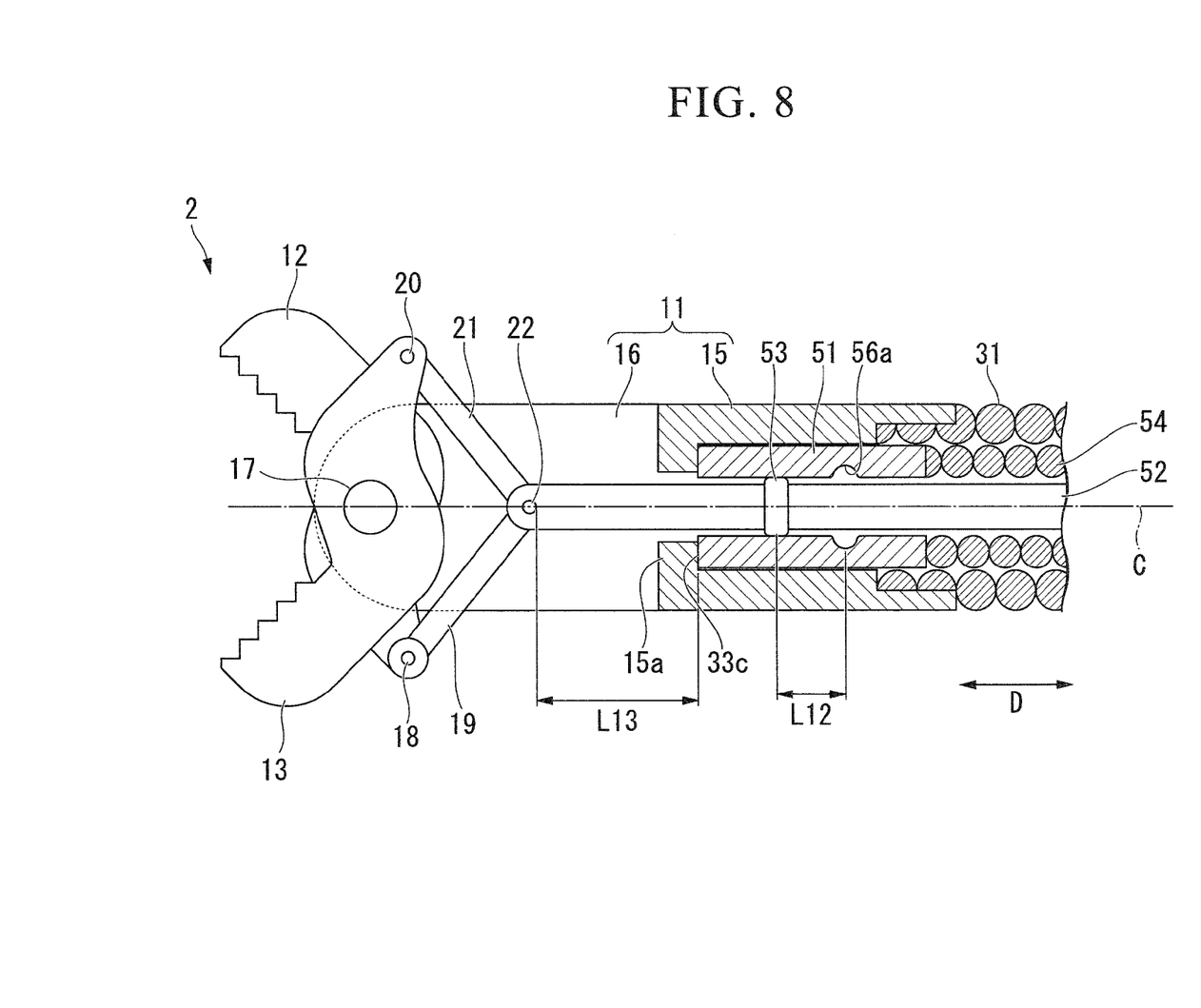
FIG. 8 is a cross-sectional view of the side surface of the distal end side in the fully open state of the grasping forceps related to the second embodiment of the present invention.

When the wire slider 63 is pressed, since the stopper 51 is engaged to the distal end cover member 11, as shown in FIG. 8, the O ring 53 is deformed so as to be radially crushed, and the manipulation wire 52 moves to the distal end side with respect to the stopper 51. Moreover, the engagement between the O ring 53 and the concave portion 56*a* is released, the elastically deformed and crushed O ring 53 slidably contacts with the inner circumferential surface of the thorough hole 56, and the grasping forceps 2 is in the fully open state. That is, by moving the manipulation wire 52 to the distal end side with respect to the stopper 51 using the moving mechanism, the position of the manipulation wire 52 with respect to the stopper 51 is moved from the above-mentioned reference position to the distal end position closer to the distal end side than the reference position. When the manipulation wire 52 is located at the distal end position, a frictional force acts between the O ring 53 and the inner circumferential surface of the through hole 56. When the manipulation wire 52 moves to the distal end position, the anti-slip surfaces 12*a* and 13*a* are separated from each other relative to the position at the time when the manipulation wire 52 is located at the reference position. For this reason, the anti-slip surfaces 12*a* and 13*a* enter the fully open state in which the opening angle of the anti-slip surfaces 12*a* and 13*a* is greater than that of the above-mentioned half-open state.

Figure 7:
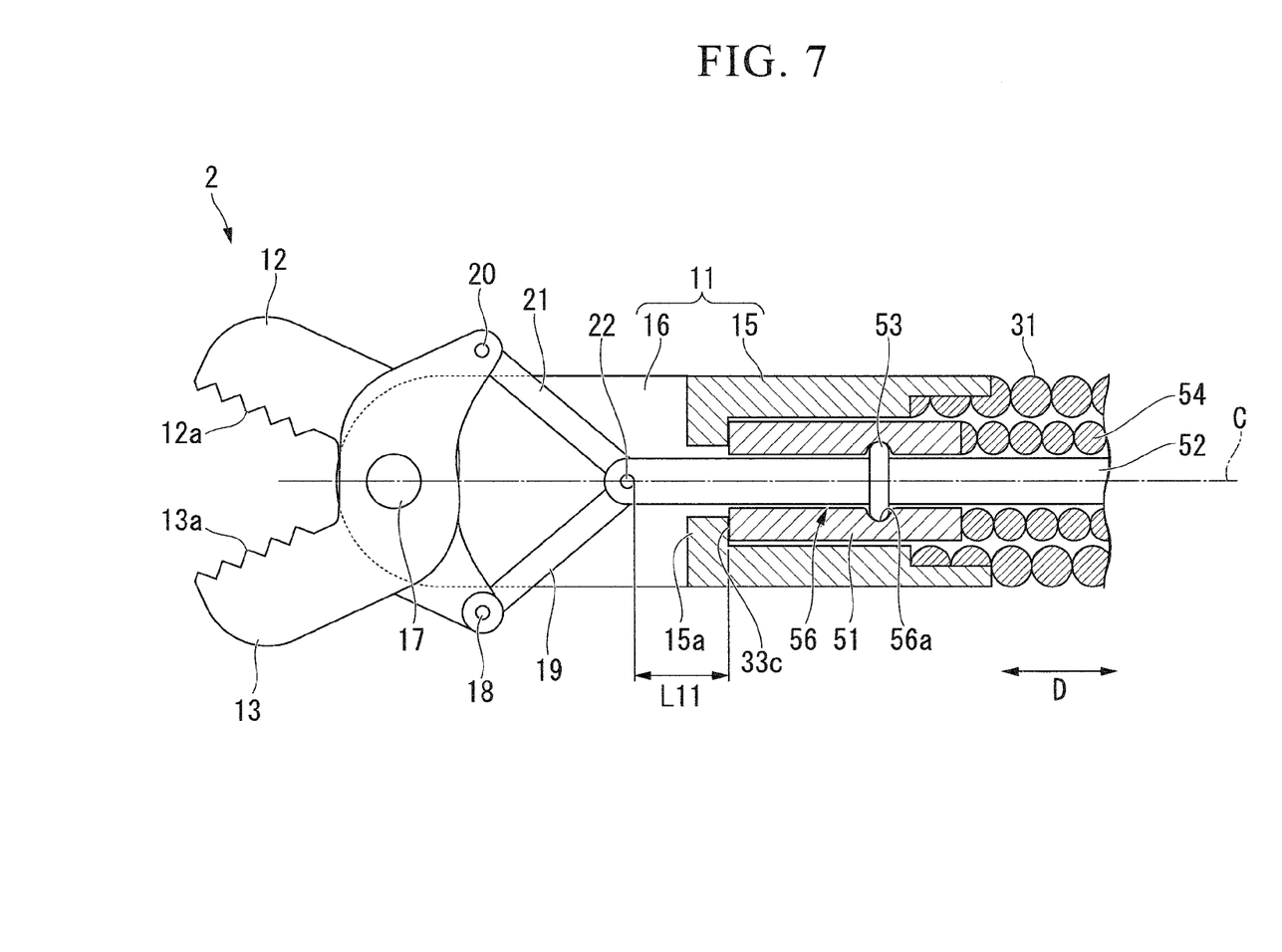
FIG. 7 is a cross-sectional view of the side surface of the distal end side in the half-open state of the grasping forceps related to the second embodiment of the present invention.

Furthermore, the length from the distal end surface 33*c* of the stopper 51 to the common rotation axis 22 in the longitudinal direction D, when engaging the stopper 51 to the engaging portion 15*a*, is a length L11 in the half-open state of FIG. 7. In contrast, as shown in FIG. 8, when the O ring 53 and the manipulation wire 52 move to the distal end side by a length L12 with respect to the concave portion 56*a*, the length from the distal end surface 33*c* to the common rotation axis 22 becomes longer like a length L13.

That is, in the case of the present embodiment, a value of which the movement length of the O ring 53 to the distal end side with respect to the concave portion 56*a* is subtracted from the length from the distal end surface 33*c* of the stopper 51 to the common rotation axis 22 is constant. For this reason, as the manipulation wire 52 moves to the distal end side, the length from the distal end surface 33*c* of the stopper 51 to the common rotation axis 22 becomes longer, and the opening angle of the anti-slip surfaces 12*a* and 13*a* increases.

In order to return the forceps members 12 and 13 of the fully open state to the half-open state, the wire slider 63 is moved to the distal end side while maintaining the position of the sheath slider 62 with respect to the manipulation portion main body 61. Then, the O ring 53 moves to the distal end side with respect to the stopper 51, the O ring 53 is engaged with the concave portion 56*a* of the stopper 51, and the anti-slip surfaces 12*a* and 13*a* enter the half-open state.

As described above, according to the grasping forceps 2 of the present embodiment, by engaging the stopper 33 to the engaging portion 15*a* in the state in which the O ring 53 is engaged with the concave portion 56*a* of the stopper 51, the anti-slip surfaces 12*a* and 13*a* can be easily controlled to be in the half-open state in which the opening angle becomes a constant value. Furthermore, by pressing the manipulation wire 52 from the half-open state, the anti-slip surfaces 12*a* and 13*a* can be set to be in the fully open state in which the opening angle is greater than that in the half-open state.

The moving mechanism is constituted by the O ring 53 formed of the elastic material, and the concave portion 56*a* of the stopper 51. For this reason, by pressing the manipulation wire 52 with respect to the stopper 51 engaged to the engaging portion 15*a* of the distal end cover member 11, the manipulation wire 52 can be positioned at a desired position in the longitudinal direction D with respect to the stopper 51 by a frictional force acting between the O ring 53 and the inner circumferential surface of the through hole 56.

The moving mechanism of the present embodiment does not need to rotate the rotary handle 42 around the axial line C like the moving mechanism of the above-mentioned first embodiment when the fully open state and the half-open state of the anti-slip surfaces 12*a* and 13*a* are switched. For this reason, it is possible to easily switch the fully open state and the half-open state of the anti-slip surfaces 12*a* and 13*a*.

The grasping forceps 2 has the inner sheath 54. For this reason, by moving the O ring 53 to the proximal end side by the wire slider 63 while maintaining the position of the stopper 51 via the inner sheath 54 using the sheath slider 62, the O ring 53 is engaged with the concave portion 56*a* of the stopper 51. In addition, by releasing the holding of the sheath slider 62 and moving the wire slider 63 to the proximal end side, the grasping forceps 2 can be returned to the closed state again.

In addition, in the present embodiment, the O ring 53 serving as the convex portion is formed on the outer circumferential surface of the manipulation wire 52, and the concave portion 56*a* is formed on the inner circumferential surface of the through hole 56 of the stopper 51. However, the concave portion may be formed on the outer circumferential surface of the manipulation wire 52, and the convex portion engaged with the concave portion may be formed on the inner circumferential surface of the through hole 56.

In the above-mentioned first and second embodiments, both forceps members 12 and 13 are set to be rotated around the rotation axis 17. However, a configuration in which one forceps member is fixed to the distal end cover member, and only the other forceps member rotates around the rotation axis may be adopted.

Furthermore, in the above-mentioned first and second embodiments, the endoscopic treatment tool is assumed to be the grasping forceps. However, the endoscopic treatment tool may be an incisional bipolar forceps, suture instruments or the like, without being limited thereto.

While preferred embodiments of the present invention have been described above, the present invention is not limited to the embodiments. Additions, omissions, substitutions, and other variations of a configuration may be made to the present invention without departing from the spirit and scope of the present invention. The present invention is not limited by the above description, and is limited only by the appended claims.

What is claimed is:

1. An endoscopic treatment tool comprising:
a longitudinal sheath having a distal end, a proximal end, a length, and a thickness that is orthogonal to the length, the sheath forming an inner cavity that extends from the distal end to the proximal end along the length of the sheath;
a support portion attached to the distal end of the sheath, the support portion comprising an engaging portion that has an annular shape and is disposed to protrude from an inner circumferential surface of the support portion;
a forceps member having a pair of facing surfaces that are supported so as to be rotatable around a rotation axis member on the support portion, the pair of facing surfaces being configured to be opened and closed and being disposed so as to protrude from the rotation axis member toward a distal end side of the endoscopic treatment tool;
a linear portion that is at least partially disposed within the cavity of the sheath and is capable of advancing and retracting along a direction of the length of the sheath to open and close the pair of facing surfaces;
a stopper that is disposed within the cavity of the sheath and is capable of advancing and retracting along the direction of the length of the sheath, the stopper being capable of restricting advancement of the linear portion when the stopper abuts against the engaging portion such that the pair of facing surfaces is retained in an open state at an opening angle; and
a moving mechanism that is configured to move at least part of the linear portion along the direction of the length of the sheath independently of the stopper by a predetermined operation of a user;
wherein:
the linear portion is configured to advance and retract along the direction of the length of the sheath together with the stopper to open and close the pair of facing surfaces until the stopper abuts against the engaging portion, and
the at least part of the linear portion is configured to advance and retract along the direction of the length of the sheath independently of the stopper to adjust a distance between a distal end of the linear portion and a distal end of the stopper when the stopper abuts against the engaging portion.

2. The endoscopic treatment tool according to claim 1, wherein:
the linear portion includes:
a first linear member that forms a distal end portion of the linear portion, a distal end of the first linear member being connected to at least one of the facing surfaces, and a proximal end of the first linear member being movably connected to the stopper, and
a second linear member that is disposed proximally of the first linear member, a distal end of the second linear member being fixed to the stopper,
the moving mechanism includes:
a male threaded portion that is formed in the proximal end of the first linear member, the male threaded portion having an axial line of the first linear member as a spiral axis, and
a female threaded portion that is formed in the distal end of the stopper, the female threaded portion being threadedly engaged with the male threaded portion,
the moving mechanism is configured to distally or proximally move the first linear portion independently of the stopper along the direction of the length of the sheath by rotating the stopper around the axial line to adjust a length of the male threaded portion that is threadedly engaged with the female threaded portion,
when the first linear portion is moved distally along the direction of the length of the sheath independently of the stopper, the distance between the distal end of the linear portion and the distal end of the stopper increases, and the length of the male threaded portion that is threadedly engaged with the female threaded portion decreases, and
when the first linear portion is moved proximally along the direction of the length of the sheath independently of the stopper, the distance between the distal end of the linear portion and the distal end of the stopper decreases, and the length of the male threaded portion that is threadedly engaged with the female threaded portion increases.

3. The endoscopic treatment tool according to claim 2, further comprising:
a first link member having a distal end and a proximal end, the distal end of the first link member being rotatably connected to a portion of one facing surface of the pair of facing surfaces, the portion of the one facing surface being disposed proximally of the rotation axis member;
a second link member having a distal end and a proximal end, the distal end of the second link member being rotatably connected to a portion of an other facing surface of the pair of facing surfaces, the portion of the other facing surface being disposed proximally of the rotation axis member; and
a second rotation axis member that rotatably connects the proximal end of the first link member and the proximal end of the second link member, wherein:
the first linear member is connected to the second rotation axis member, and the stopper has a contact surface that comes into contact with a surface of the engaging portion when the stopper abuts against the engaging portion.

4. The endoscopic treatment tool according to claim 2, wherein:
the opening angle of the pair of facing surfaces in the open state is set to be a predetermined value when the linear portion is moved proximally to a reference position at which the distance between the distal end of the linear portion and the distal end of the stopper is decreased to a minimum value; and
the opening angle of the pair of facing surfaces in the open state is increased to be larger than the predetermined value when the linear portion is moved distally with respect to the reference position such that the distance between the distal end of the linear portion and the distal end of the stopper is increased.

5. The endoscopic treatment tool according to claim 1, wherein:
the stopper includes a through hole which penetrates in the direction of the length of the sheath and through which the linear portion is inserted,
the moving mechanism has:
a concave portion that is formed on one of an outer circumferential surface of the linear portion and an inner circumferential surface of the through hole, and
a convex portion that is formed on an other of the outer circumferential surface of the linear portion and the inner circumferential surface of the through hole,
the convex portion is configured to engage with the concave portion,
the linear portion is configured to move along the direction of the length of the sheath independently of the stopper when at least a predetermined amount of force is applied to the stopper and the linear portion along the direction of the length of the sheath and the stopper abuts against the engaging portion,
the convex portion is configured to be elastically deformed such that the convex portion is not engaged with the concave portion when the linear portion is moved along the direction of the length of the sheath independently of the stopper,
the convex portion is configured to be in sliding contact with the one of the outer circumferential surface of the linear portion and the inner circumferential surface of the through hole when the convex portion is not engaged with the concave portion,
a distal end portion of the linear portion is in a reference position with respect to the stopper when the concave portion is engaged with the convex portion, and
the distal end portion of the linear portion is in a distal end position with respect to the stopper when the linear portion is moved along the direction of the length of the sheath toward the distal end side of the endoscopic treatment tool independently of the stopper such that the convex portion is not engaged with the concave portion.

6. The endoscopic treatment tool according to claim 5, further comprising: an inner sheath that extends proximally from a proximal end of the stopper.

7. The endoscopic treatment tool according to claim 5, further comprising:
a first link member having a distal end and a proximal end, the distal end of the first link member being rotatably connected to a portion of one facing surface of the pair of the facing surfaces, the portion of the one facing surface being disposed proximally of the rotation axis member;
a second link member having a distal end and a proximal end, the distal end of the second link member being rotatably connected to a portion of an other facing surface of the pair of facing surfaces, the portion of the other facing surface being disposed proximally of the rotation axis member; and
a second rotation axis member that rotatably connects the proximal end of the first link member and the proximal end of the second link member,
wherein:
the distal end of the linear portion is connected to the second rotation axis member,
the stopper has a contact surface that comes into contact with a surface of the engaging portion when the stopper abuts against the engaging portion, and
a distance from the second rotation axis member to the contact surface of the stopper increases as the distal end of the linear portion moves toward the distal end side of the endoscopic treatment tool.

8. The endoscopic treatment tool according to claim 1, wherein:
the linear portion includes:
a first linear member that forms a distal end portion of the linear portion, a distal end of the first linear member being connected to at least one of the facing surfaces, and a proximal end of the first linear member being connected to the stopper, and
a second linear member that is disposed proximally of the first linear member, a distal end of the second linear member being fixed to the stopper,
the moving mechanism includes:
a male threaded portion that is formed in the proximal end of the first linear member, the male threaded portion having an axial line of the first linear member as a spiral axis, and
a female threaded portion that is formed in the distal end of the stopper, the female threaded portion being threadedly engaged with the male threaded portion,
the moving mechanism is configured to move the first linear portion distally with respect to the stopper along the direction of the length of the sheath by rotating the stopper around the axial line to adjust a length of the male threaded portion that is threadedly engaged with the female threaded portion,
the distance between the distal end of the linear portion and the distal end of the stopper is decreased when the length of the male threaded portion that is threadedly engaged with the female threaded portion is increased, and
the distance between the distal end of the linear portion and the distal end of the stopper is increased when the length of the male threaded portion that is threadedly engaged with the female threaded portion is decreased.

* * * * *